United States Patent
Dunning

(10) Patent No.: US 9,486,271 B2
(45) Date of Patent: Nov. 8, 2016

(54) METHOD AND APPARATUS FOR IDENTIFICATION USING CAPACITIVE ELEMENTS

(75) Inventor: James E. Dunning, Lafayette, CO (US)

(73) Assignee: COVIDIEN LP, Mansfield, MA (US)

(*) Notice: Subject to any disclaimer, the term of this patent is extended or adjusted under 35 U.S.C. 154(b) by 706 days.

(21) Appl. No.: 13/411,722

(22) Filed: Mar. 5, 2012

(65) Prior Publication Data

US 2013/0231656 A1 Sep. 5, 2013

(51) Int. Cl.
| | |
|---|---|
| A61B 18/12 | (2006.01) |
| A61B 18/04 | (2006.01) |
| A61B 18/00 | (2006.01) |
| A61B 17/00 | (2006.01) |

(52) U.S. Cl.
CPC .......... *A61B 18/1206* (2013.01); *A61B 90/90* (2016.02); *A61B 90/98* (2016.02); *A61B 18/04* (2013.01); *A61B 2017/00482* (2013.01); *A61B 2018/00178* (2013.01); *A61B 2018/00988* (2013.01); *A61B 2090/0814* (2016.02)

(58) Field of Classification Search
CPC .................................. A61B 19/44–2019/448
USPC .......................................................... 606/27
See application file for complete search history.

(56) References Cited

U.S. PATENT DOCUMENTS

| | | | |
|---|---|---|---|
| 5,400,267 A | 3/1995 | Denen et al. | |
| 5,444,223 A * | 8/1995 | Blama ................ | G06K 19/0672 235/435 |
| 5,529,235 A | 6/1996 | Boiarski et al. | |
| 5,535,934 A | 7/1996 | Boiarski et al. | |
| 5,535,937 A | 7/1996 | Boiarski et al. | |
| 5,562,239 A | 10/1996 | Boiarski et al. | |
| 5,693,042 A | 12/1997 | Boiarski et al. | |
| 6,068,627 A | 5/2000 | Orszulak et al. | |
| 6,074,386 A | 6/2000 | Goble et al. | |
| 6,283,961 B1 | 9/2001 | Underwood et al. | |
| 6,402,743 B1 | 6/2002 | Orszulak et al. | |
| 6,497,659 B1 | 12/2002 | Rafert | |
| 6,685,701 B2 | 2/2004 | Orszulak et al. | |
| 6,783,523 B2 | 8/2004 | Qin et al. | |
| 6,843,789 B2 | 1/2005 | Goble | |
| 6,893,435 B2 | 5/2005 | Goble | |
| 6,977,495 B2 | 12/2005 | Donofrio | |
| 7,044,949 B2 | 5/2006 | Orszulak et al. | |

(Continued)

FOREIGN PATENT DOCUMENTS

| | | |
|---|---|---|
| DE | 4339049 A1 | 5/1995 |
| EP | 2 147 651 A1 | 1/2010 |
| WO | WO 97/24073 | 7/1997 |

OTHER PUBLICATIONS

"Capacitive Reactance," accessed Mar. 11, 2015, Electronics Tutorials, http://www.electronics-tutorials.ws/filter/filter_1.html.*
International Search Report dated Jul. 18, 2013 in International Application No. PCT/US2013/028264.
Extended European Search Report from Appl. No. 13757352.3 dated Septeber 22, 2015.
Chinese Office Action from Appl. No. CN 201380012875.7 dated Mar. 23, 2016.

*Primary Examiner* — Michael Kahelin

(57) ABSTRACT

A surgical instrument and related method are provided. The surgical instrument includes a housing, a cable, and an identifying circuit. An end-effector is coupled to the housing for treating tissue. The cable extends from the housing and is configured to couple the surgical instrument to a generator. The identifying circuit includes a plurality of capacitive elements disposed on the surgical instrument. The plurality of capacitive elements is readable by the generator.

10 Claims, 9 Drawing Sheets

(56) References Cited

U.S. PATENT DOCUMENTS

| | | |
|---|---|---|
| 7,214,224 B2 | 5/2007 | Goble |
| 7,736,358 B2 | 6/2010 | Shores et al. |
| 2003/0139741 A1 | 7/2003 | Goble et al. |
| 2004/0054365 A1 | 3/2004 | Goble |
| 2004/0267297 A1 | 12/2004 | Malackowski |
| 2005/0027311 A1 | 2/2005 | Wiener et al. |
| 2008/0129527 A1 | 6/2008 | Ohyama et al. |
| 2009/0065565 A1 | 3/2009 | Cao |
| 2009/0090763 A1 | 4/2009 | Zemlok et al. |
| 2010/0023008 A1 | 1/2010 | Heard et al. |
| 2010/0121320 A1* | 5/2010 | Hosier ............ A61B 18/1206 606/42 |
| 2010/0262134 A1 | 10/2010 | Jensen et al. |
| 2010/0305563 A1 | 12/2010 | Varney |

\* cited by examiner

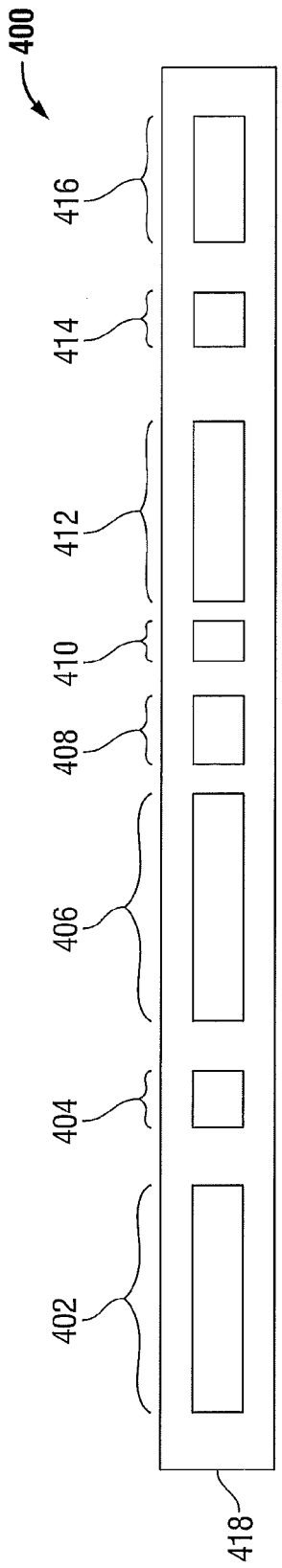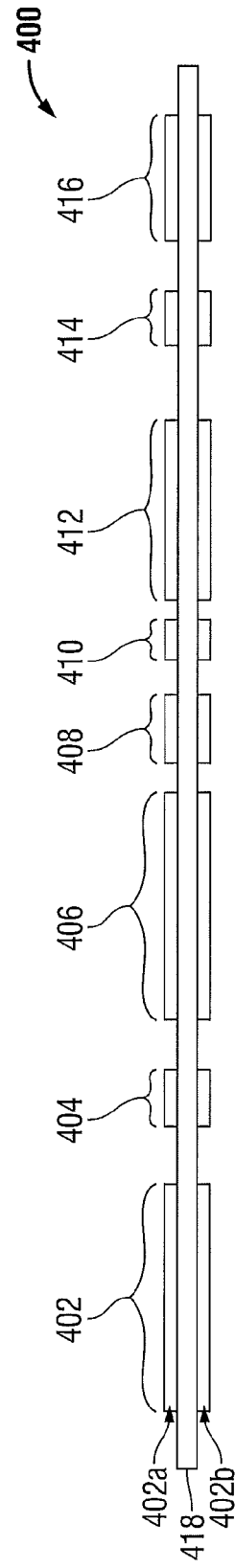
FIG. 5A
FIG. 5B

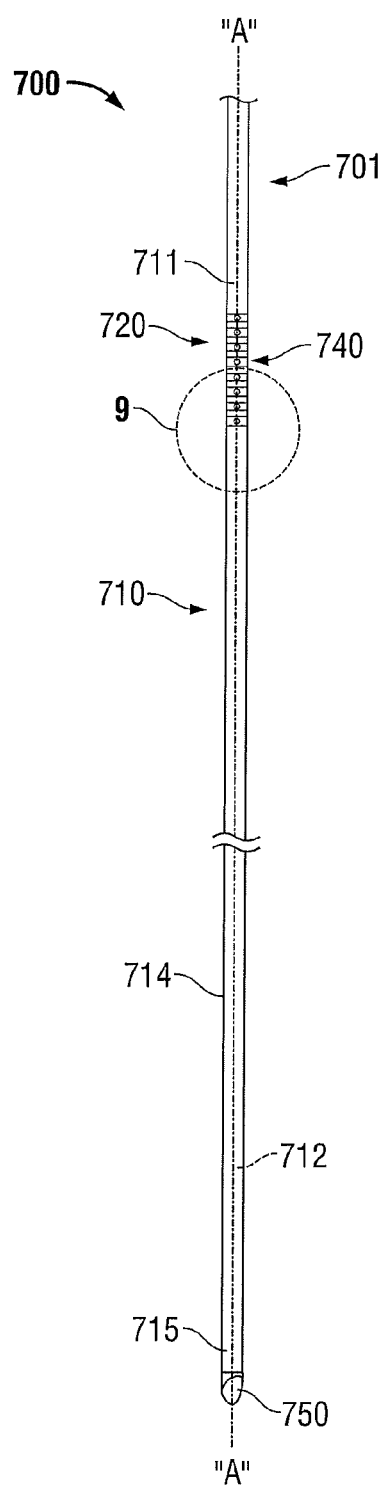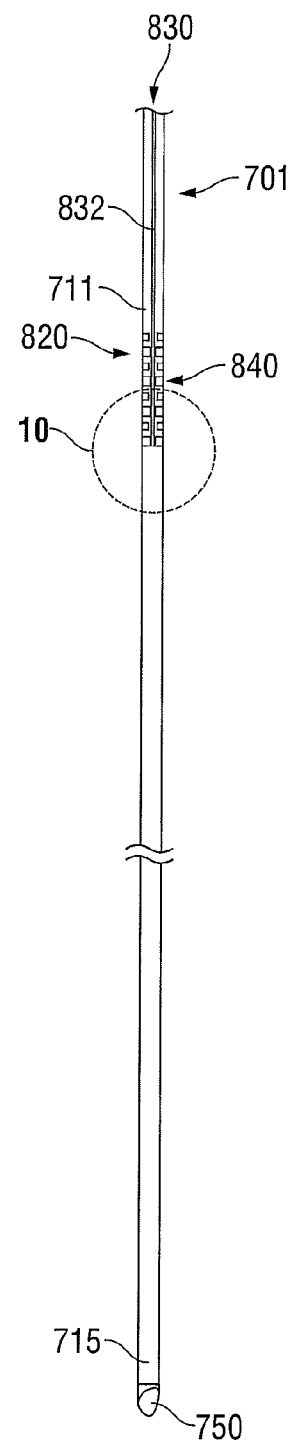
FIG. 7                    FIG. 8

METHOD AND APPARATUS FOR IDENTIFICATION USING CAPACITIVE ELEMENTS

BACKGROUND

1. Technical Field

The present disclosure relates to surgical instruments. More particularly, the present disclosure relates to a method, system, and apparatus for identifying surgical instruments using capacitive elements.

2. Discussion of Related Art

Energy-based tissue treatment is well known in the art. Various types of energy (e.g., electrical, ultrasonic, microwave, cryogenic, heat, laser, etc.) are used to treat tissue. One such type of energy used to treat tissue is electrosurgical energy. Electrosurgery is the application of electricity and/or electromagnetic energy to cut, dissect, ablate, coagulate, cauterize, seal or otherwise treat biological tissue during a surgical procedure. Generally, electrosurgery utilizes an electrosurgical generator operable to output energy and active and return electrodes that are electrically connected via a cable assembly to the generator.

In bipolar electrosurgery, one of the electrodes of a hand-held instrument functions as the active electrode and another electrode of the hand-held instrument functions as the return electrode. The return electrode is placed in close proximity to the active electrode such that an electrical circuit is formed between the two electrodes (e.g., electrosurgical forceps). Bipolar electrosurgical techniques and instruments can be used to coagulate blood vessels or tissue, e.g., soft tissue structures, such as lung, brain, and intestine. A surgeon can cauterize, coagulate, desiccate tissue, or simply reduce or slow bleeding by controlling the intensity, frequency, and duration of the electrosurgical energy applied between the electrodes and through the tissue. In order to achieve the desired surgical effects without causing unwanted charring of tissue at the surgical site or causing collateral damage to adjacent tissue, e.g., thermal spread, the output from the electrosurgical generator is controlled, e.g., power, waveform, voltage, current, pulse rate, etc.

In monopolar electrosurgery, the active electrode is typically part of the surgical instrument held by the surgeon that is applied to the tissue to be treated. A patient return pad having one or more return electrodes is placed remotely from the active electrode to carry the electrosurgical energy back to the generator and safely disperse current applied by the active electrode. The return electrodes usually have a large patient-contact surface area to minimize heating at that site. Heating is caused by high current densities that directly depend on the surface area. A larger surface contact area results in lower localized heat intensity. The size of the return electrodes is typically chosen based upon assumptions of the maximum current utilized during a particular surgical procedure and the generator's duty cycle (i.e., the percentage of time the generator is on).

Electrosurgical devices utilizing electricity and/or electromagnetic energy have been developed for a variety of uses and applications. One type of energy-based treatment of tissue is microwave-energy based treatment. Typically, microwave apparatus for use in surgical procedures include a microwave generator that functions as an energy source, and a microwave surgical instrument (e.g., microwave ablation probe) having an antenna assembly for directing energy to the target tissue. The microwave generator and surgical instrument are typically operatively coupled by a cable assembly having a plurality of conductors for transmitting microwave energy from the generator to the instrument, and for communicating control, feedback and identification signals between the instrument and the generator.

There are several types of microwave surgical instruments (e.g., microwave probes) in use, e.g., monopole, dipole, and helical. One type is a monopole antenna probe, which consists of a single, elongated microwave conductor exposed at the end of the probe. The probe is typically surrounded by a dielectric sleeve. The second type of microwave probe commonly used is a dipole antenna, which typically consists of a coaxial construction having an inner conductor and an outer conductor with a dielectric junction separating a portion of the inner conductor. In the monopole and dipole antenna probes, microwave energy generally radiates perpendicularly from the axis of the conductor.

SUMMARY

According to an aspect, a surgical instrument is provided. The surgical instrument may be an electrosurgical instrument, a microwave surgical instrument, and/or an ultrasonic surgical instrument. The surgical instrument includes a housing, a cable, and an identifying circuit. An end-effector is coupled to the housing for treating tissue. The cable extends from the housing and is configured to couple the surgical instrument to a generator. The identifying circuit includes a plurality of capacitive elements disposed on the surgical instrument. The plurality of capacitive elements is readable by the generator. A capacitance-to-digital converter may be electrically coupled to the identifying circuit to interrogate the identifying circuit.

According to another aspect of the present disclosure, each of the plurality of capacitive elements corresponds to a number or an alphanumeric character. Each of the capacitive elements has a capacitance, and a plurality of capacitive ranges corresponds to a plurality of numbers. Each of the capacitive elements is within a capacitive range of the plurality of capacitive ranges and thereby corresponds to a number that corresponds to the range. In some embodiments of the present disclosure, an electrically-conductive ink disposed on a substrate defines the plurality of capacitive elements.

According to another aspect of the present disclosure, the identifying circuit electrically communicates with a multiplexer to separately couple to each of the plurality of capacitive elements for interrogation.

According to an aspect of the present disclosure, a method for identifying a surgical instrument is provided. The method includes the steps of connecting the surgical instrument to a generator, interrogating a capacitive element within the surgical instrument, and identifying the surgical instrument based upon the capacitive element. The capacitive elements may be individually interrogated. The method may include the steps of interrogating a plurality of capacitive elements including the capacitive element within the surgical instrument, and mapping each of the capacitive elements to a corresponding number. The plurality of capacitive elements corresponds to a plurality of numbers, and the plurality of numbers forms a surgical instrument identification value. The interrogating step may determine the capacitance of one or more capacitive elements using a capacitance-to-digital converter.

The method may further include, in some embodiments, the steps of performing a hash algorithm on the surgical instrument identification value, and comparing the hashed surgical instrument identification value to values within a database. Additionally or alternatively, the method may perform other encryption methodologies, e.g., Advanced Encryption Standard (AES). The method also includes, in some embodiments, the step of determining a manufacturing lot number of the surgical instrument corresponding to the capacitive element. The method may further include the step of determining if the surgical instrument is an authorized surgical instrument based upon the comparison between the hashed surgical instrument identification value and the values within the database. Additionally or alternatively, the method may include determining if an end-of-life has been achieved of the surgical instrument corresponding to the capacitive element. The method may include the step of disabling the generator in response to the identified surgical instrument and/or the end-of-life determination.

BRIEF DESCRIPTION OF THE DRAWINGS

Objects and features of the presently-disclosed method, system, and apparatus for identifying surgical instruments using capacitive elements will become apparent to those of ordinary skill in the art when descriptions of various embodiments thereof are read with reference to the accompanying drawings, of which:

FIG. 5A is a top view of the identifying circuit of FIG. 4 formed by depositing silver ink on a substrate;

FIG. 5B is a side view of the identifying circuit of FIG. 5A;

FIG. 7 is a schematic diagram of a microwave surgical instrument including an identifying circuit according to an embodiment of the present disclosure;

FIG. 8 is a schematic diagram of a microwave surgical instrument including an identifying circuit according to another embodiment of the present disclosure;

DETAILED DESCRIPTION

Figure 1:
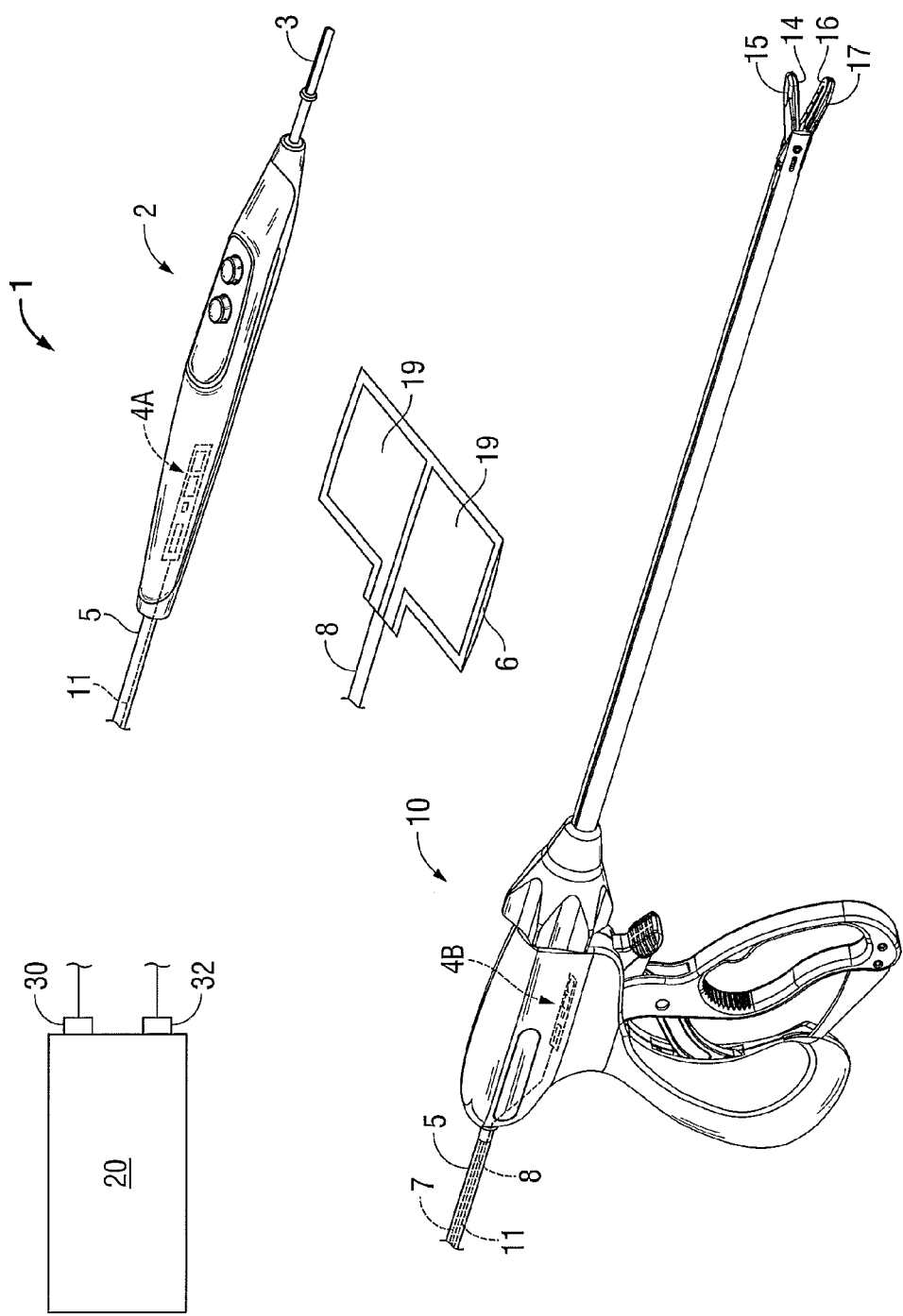
FIG. 1 is a schematic diagram of an electrosurgical system according to an embodiment of the present disclosure.

Hereinafter, embodiments of a method, system, and apparatus for identifying surgical instruments using capacitive elements of the present disclosure are described with reference to the accompanying drawings. Like reference numerals may refer to similar or identical elements throughout the description of the figures. In the following description, well-known functions or constructions are not described in detail to avoid obscuring the present disclosure in unnecessary detail.

FIG. 1 is a schematic illustration of a bipolar and monopolar electrosurgical system 1 according to an embodiment of the present disclosure. The system 1 includes a surgical generator 20. The surgical generator 20 according to the present disclosure can perform energy-based surgical procedures. In some of the embodiments disclosed herein, the surgical generator 20 is described as an electrosurgical generator; however, it is to be appreciated that a microwave surgical generator or an ultrasonic surgical generator or other suitable generator may be used in the place of the electrosurgical generator where appropriate in the various embodiments disclosed herein.

The surgical generator 20 may include a plurality of outputs for interfacing with various surgical instruments such as electrosurgical instruments, e.g., monopolar active electrode, return electrode, bipolar electrosurgical forceps, footswitch, etc. The surgical generator 20 generally includes electronic circuitry configured to generate radio frequency power specifically suited for various energy-based surgical procedures such as electrosurgical modes (e.g., cutting, blending, division, etc.) and procedures (e.g., monopolar, bipolar, vessel sealing).

The system 1 includes one or more monopolar electrosurgical instruments 2 having one or more electrodes 3 (e.g., an electrosurgical pencil, an electrosurgical cutting probe, ablation electrode(s), etc.) for treating tissue of a patient. The monopolar electrosurgical instrument 2 includes an identifying circuit 4A disposed in association with the monopolar electrosurgical instrument 2. Although one identifying circuit 4A is shown in FIG. 1, one or more identifying circuits 4A may be disposed in association with one or more surfaces of the monopolar electrosurgical instrument 2, or component thereof. In some embodiments, one or more identifying circuits may be disposed in association with one or more interior surfaces and/or one or more exterior surfaces of the monopolar electrosurgical instrument 2, or component thereof. The generator 20 can identify the monopolar electrosurgical instrument 2 by interrogating the identifying circuit 4A, e.g., via a cable 11 within a supply line 5. The cable 11 includes one or more electrically-conductive wires (not shown in FIG. 1). In some embodiments, the generator 20 supplies electrosurgical RF energy to the instrument 2. The instrument 2 includes an active electrode 3 that is connected via a supply line 5 to an active terminal 30 of the generator 20, allowing the instrument 2 to coagulate, ablate, or otherwise treat tissue. The energy is returned to the generator 20 through a return pad 6 via a return line 8 at a return terminal 32 of the generator 20.

The return pad 6 may include a plurality of return electrodes 19 that are arranged to minimize the chances of tissue damage by maximizing the overall contact area with the patient. In addition, the generator 20 and the return pad 6 may be configured for monitoring so-called "tissue-to-patient" contact to ensure that sufficient contact exists therebetween to further minimize chances of tissue damage.

In some embodiments, as shown in FIG. 1, the system 1 includes bipolar electrosurgical forceps 10 having one or more electrodes for treating tissue of a patient. The bipolar electrosurgical forceps 10 include an identifying circuit 4B that is interrogated by the generator 20 to identify the bipolar electrosurgical forceps 10. The electrosurgical forceps 10 may be interrogated by the generator 20 via the cable 11. The electrosurgical forceps 10 includes opposing jaw members 15, 17 having one or more active electrodes 14 and a return electrode 16 disposed therein, respectively. The one or more active electrodes 14 and the return electrode 16 are connected to the generator 20 through a cable 11 that includes the supply and return lines 7, 8 coupled to the active and return terminals 30, 32, respectively. In some embodiments, the electrosurgical forceps 10 is coupled to the generator 20 at a connector (not shown) having connections to the active and return terminals 30, 32 (e.g., pins) via a plug disposed at the end of the cable 18, wherein the plug includes contacts from the supply and return lines 7, 8. The generator 20 can interrogate the identifying circuit 4B to identify the electrosurgical forceps 10.

Figure 2:
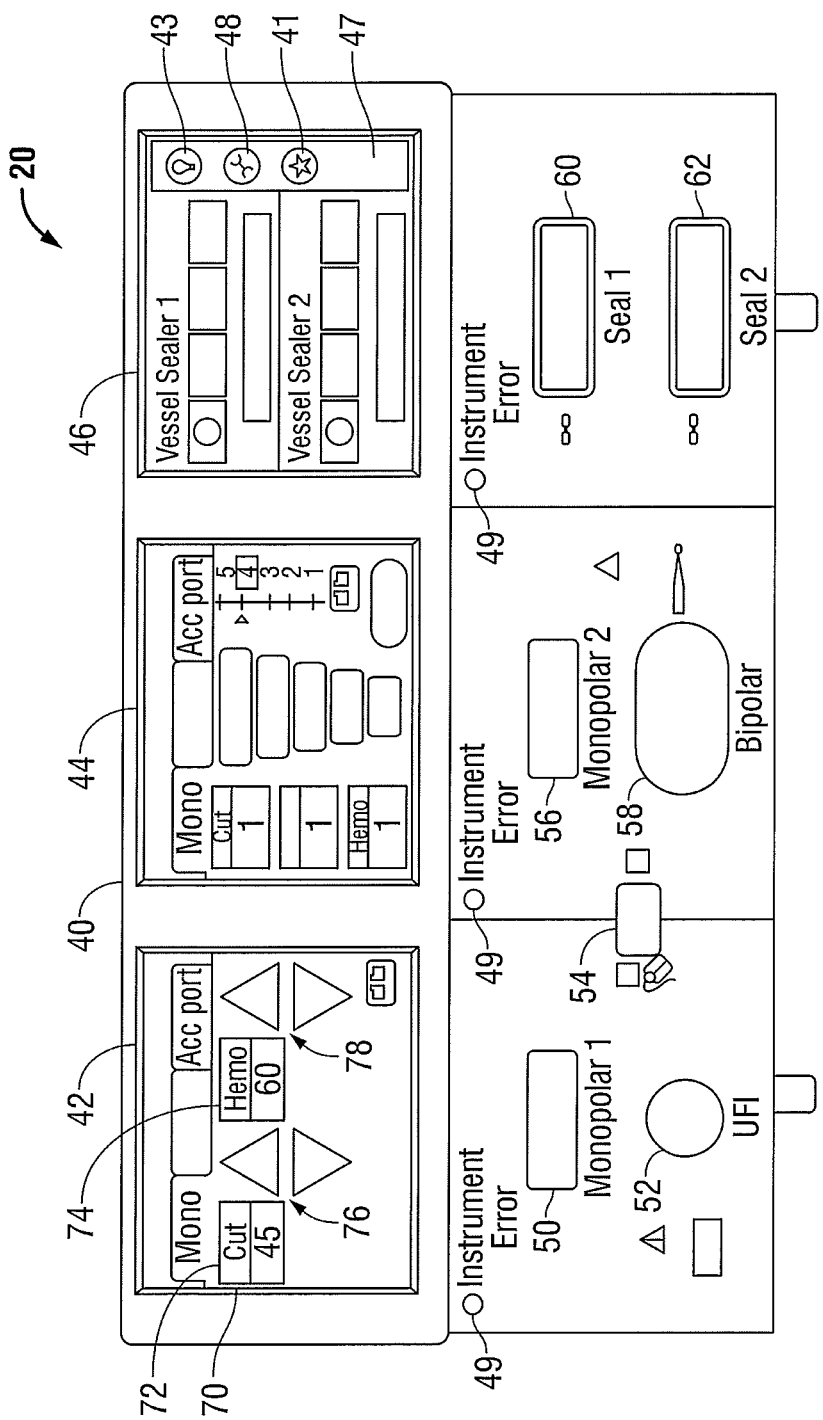
FIG. 2 is a front view of the generator of FIG. 1 according to an embodiment of the present disclosure.

With reference to FIG. 2, a front face 40 of the generator 20 is shown. The generator 20 may be any suitable type (e.g., electrosurgical, ultrasonic, light, optical, microwave, etc.). The generator 20 may include a plurality of connectors, e.g., seven connectors 50, 52, 54, 56, 58, 60 and 62, to accommodate various types of electrosurgical instruments (e.g., monopolar electrosurgical instruments 2, electrosurgical forceps 10, etc.). The generator 20 includes one or more display screens 42, 44, 46 for providing the user with a variety of output information, e.g., intensity settings, treatment complete indicators, etc. Each of the screens 42, 44, 46 is generally associated with one or more of the plurality of connectors 50, 52, 54, 56, 58, 60 and 62. The generator 20 includes suitable input controls (e.g., buttons, activators, switches, touch screen, etc.) for controlling the generator 20. The display screens 42, 44, and 46 may be configured as touch screens that display a corresponding menu for the electrosurgical instruments (e.g., multiple instruments 2, electrosurgical forceps 10, etc.). The user makes inputs by touching corresponding menu options. The controls allow the user to select desired output modes as well as adjust operating parameters of the modes, such as power, waveform parameters, etc., to achieve the desired output suitable for a particular task, e.g., cutting, coagulating, tissue sealing, etc.

Referring now to FIGS. 1 and 2, the generator 20 interrogates any surgical instrument connected to a corresponding connector 50, 52, 54, 56, 58, 60 or 62, such as the monopolar electrosurgical instrument 2 or the bipolar electrosurgical forceps 10. The generator 20 interrogates one or more capacitive elements within a respective identifying circuit (e.g., identifying circuit 4A or 4B shown in FIG. 1 or identifying circuit 14 shown in FIG. 3) of a respective surgical instrument, e.g., monopolar electrosurgical instrument 2 or bipolar electrosurgical forceps 10. The generator 20 identifies a respective surgical instrument based upon the capacitances of the capacitive elements. In some embodiments, the generator 20 includes instrument-error indicator lights 49. One or more of the error indicator lights 49 may be light emitting diodes. A respective indictor light 49 may turn on in response to the identification of a respective surgical instrument plugged into a connector 50, 52, 54, 56, 58, 60 or 62, e.g., an unauthorized surgical device may be connected to one of the connectors 50, 52, 54, 56, 58, 60 and 62. In some embodiments, one or more of the display screens 42, 44 and 46 may additionally, or alternatively, be used to convey information associated with the identification of a surgical instrument plugged into a connector 50, 52, 54, 56, 58, 60 or 62.

The generator 20 is configured to operate in a variety of modes. In one embodiment, the generator 20 may output various modes, e.g., cut, blend, division of tissue with hemostasis, fulgurate, and/or spray. In some embodiments, each of the modes operates based on a preprogrammed power curve that dictates how much power is outputted by the generator 20 at varying impedance ranges of the load (e.g., tissue). Each of the power curves includes a constant power, constant voltage, and constant current ranges that are defined by the user-selected power setting and the measured minimum impedance of the load.

The screen 46 controls bipolar sealing procedures performed by the forceps 10 that may be plugged into the connectors 60, 62. The generator 20 outputs energy through the connectors 60, 62 suitable for sealing tissue grasped by the forceps 10. The screen 46 also controls a system tray 47 to allow the user to access and adjust system settings. The system tray 47 may include a brightness icon 43. The system tray 47 may include a menu icon 48. The system tray 47 may include an error-disabled icon 41. The brightness icon 43 allows the user to adjust the brightness of the screens 42, 44, 46. The error disabled icon 41 indicates that the error warnings have been disabled using the service menu. The menu icon 48 allows access to the main menu where the user can change options for language, appearance, and other operations.

The screen 42 controls monopolar output and the devices connected to the connectors 50 and 52. In some embodiments, the connector 50 is configured to couple to the instrument 2, and the connector 52 may be configured to couple to a foot switch (not shown), which provides for additional inputs (e.g., replicating inputs of the generator 20 and/or instrument 2). For example, in standard monopolar mode, the power output modes 72, 74 are indicted on interface 70. The user adjusts the power controls using up and down arrows 76, 78 for each mode respectively.

The screen 44 controls monopolar and bipolar output and the devices connected to the connectors 56 and 58. Connector 56 is configured to couple to the instrument 2, allowing the generator 20 to power multiple instruments 2. Connector 58 is configured to couple to a bipolar instrument. When using the generator 20 in monopolar mode (e.g., with instruments 2), the return electrode 6 is coupled to the connector 54, which is associated with the screens 42, 44.

Figure 3:
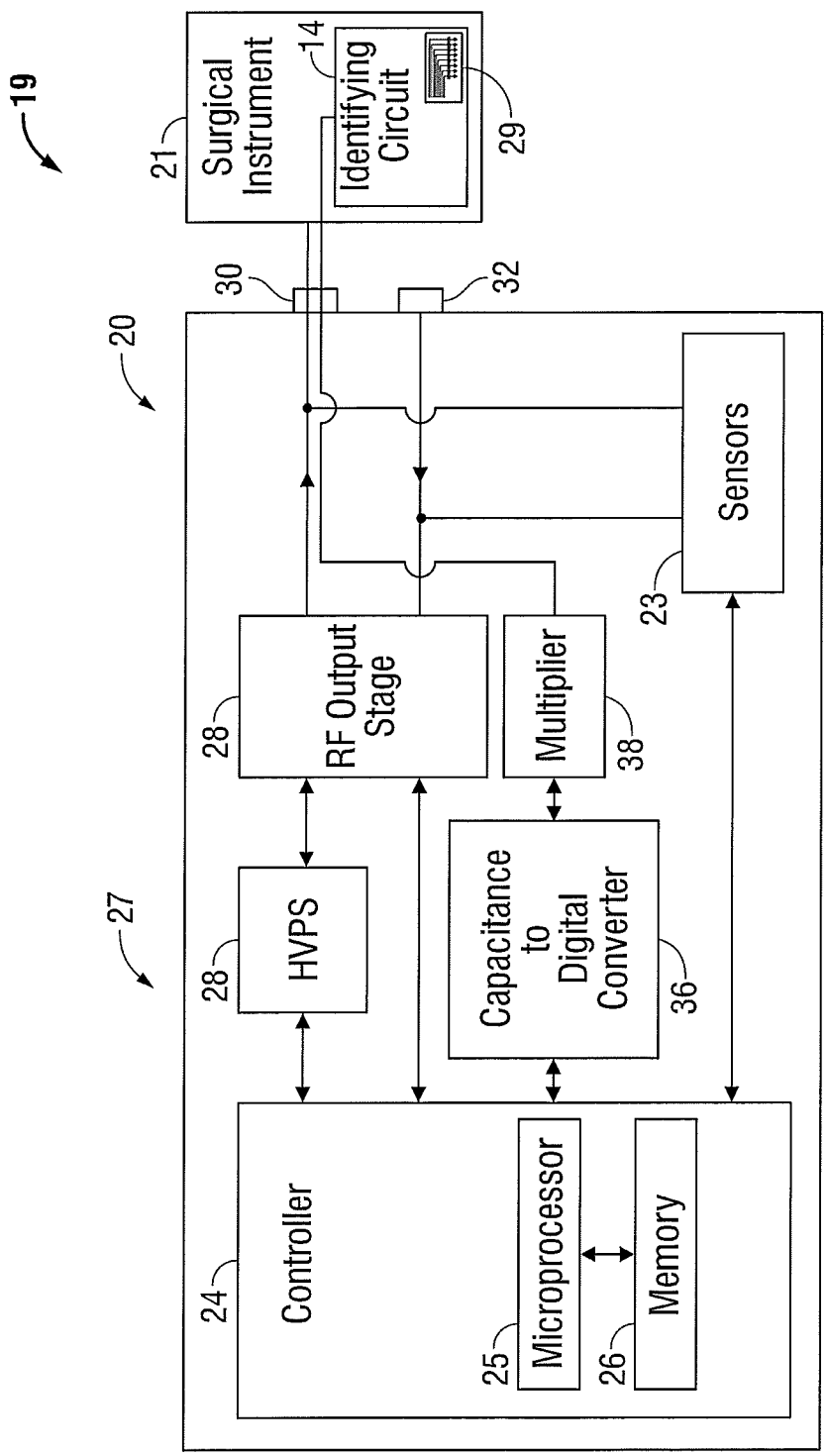
FIG. 3 is a schematic block diagram of an electrosurgical system according to an embodiment of the present disclosure.

FIG. 3 shows a schematic block diagram of an electrosurgical system 19 including the generator 20 coupled to a surgical instrument 21. The generator includes a controller 24, a high voltage DC power supply 27 ("HVPS") and an RF output stage 28, a capacitance-to-digital converter 36, and a multiplexer 38. The instrument 21 includes an identifying circuit 14. The instrument 21 may be the monopolar surgical instrument 2 or the bipolar electrosurgical forceps 10 of FIG. 1.

The HVPS 27 is connected to an AC source (e.g., an electrical wall outlet) and provides high voltage DC power to an RF output stage 28, which then converts high voltage DC power into RF energy and delivers the RF energy to the port or active terminal 30. The electrosurgical energy is returned thereto via the port or return terminal 32, e.g., the electrosurgical energy may be returned through a return pad (not shown). In particular, the RF output stage 28 generates sinusoidal waveforms of high RF energy. The RF output stage 28 is configured to operate in a plurality of modes, during which the generator 20 outputs corresponding waveforms having specific duty cycles, peak voltages, crest factors, etc. In another embodiment, the generator 20 may be based on other types of suitable power supply topologies.

The controller 24 includes a processing unit 25 in operable communication with a memory 26, which may be volatile type memory, e.g., RAM, and/or non-volatile type memory, e.g., flash media, disk media, etc. The processing unit 25 includes an output port that is operably connected to the HVPS 27 and the RF output stage 28 allowing the processing unit 25 to control the output of the generator 20 according to either an open-loop control scheme or a closed-loop control scheme. The processing unit 25 may include any type of computing device, computational circuit, or any type of processor or processing circuit capable of executing a series of instructions that are stored in a memory. The processing unit 25 may include multiple processors and/or multicore CPUs and may include any type of processor, such as a microprocessor, digital signal processor, microcontroller, or the like, adapted to perform the calculations discussed herein.

The controller 24 is coupled to the capacitance-to-digital converter 36 which is, in turn, coupled to multiplexer 38. The multiplexer 38 is coupled to the surgical instrument 21 such that the capacitance-to-digital converter 36 measures the capacitance of one or more capacitive elements 29 within the identifying circuit 14 to identify the surgical instrument 21.

Each of the capacitive elements 29 has a capacitance. The multiplexer 38 individually selects one of the capacitive elements 29 for interrogation so that the capacitance-to-digital converter 36 can measure its respective capacitance. The capacitance-to-digital converter 36 digitally communicates the measured capacitances to the controller 24. The controller 24 maps each capacitance of the capacitive elements 29 to a corresponding number. For example, 16 different capacitive ranges may correspond to 16 different hexadecimal numbers, e.g., made of digits 0 . . . 9 and A . . . F. Eight of capacitive elements 29 may correspond to 4,294,967,296 values when represented by an 8-digit hexadecimal number. The mapped values can correspond to a number that is used as an identification value for the surgical instrument 21, e.g., a surgical instrument identification value may be the sequential aggregation of the mapped numbers (or concatenation of the mapped numbers). In some embodiments, a hash algorithm is performed on the surgical instrument identification value to securely identify the surgical instrument 21. The hash algorithm may be Message Digest 5 (MD5), or a Secure Hash Algorithm (SHA), e.g., SHA-0, SHA-1, or SHA-2, or the like. The hashed surgical instrument identification value may be compared to values within a database, e.g., within memory 26, to determine if the surgical instrument 21 is authorized. In some embodiments, the controller 24 disables the generator 20, e.g., by preventing the RF output stage 28 from supplying energy to the surgical instrument 21, if it is determined that an unauthorized surgical instrument 21 is coupled to the generator 20. Additionally or alternatively, other encryption methodologies, e.g., Advanced Encryption Standard (AES), may be performed.

The surgical instrument identification value may additionally, or alternatively, be used to keep track of the number of times the surgical instrument 21 has been used. In some embodiments, the generator 20 is adapted to determine if an end-of-life of the surgical instrument 21 has been reached, e.g., by comparing the stored number of times the surgical instrument 21 has been used to a predetermined threshold. In some cases, where the surgical instrument 21 may be a single-use disposable instrument, the generator 20 may use the surgical instrument identification value to determine if the surgical instrument 21 has been previously used. If so, the generator 20 may be adapted to prevent the surgical instrument 21 from being used again.

The surgical instrument identification value may correspond to a serial number of the surgical instrument 21, a lot number of the surgical instrument 21, a type of instrument of the surgical instrument 21, and/or the like. The identifying circuit 14 may include multiple values for determining one or more parameters of the surgical instrument 21.

The surgical generator 20 receives feedback from one or more sensors 23 to form a closed-loop control system (not shown) within the controller 21. The control system within the controller 24 may be adjusted based upon the identification of the surgical instrument 21. The one or more sensors 23 measure a variety of tissue and energy properties (e.g., tissue impedance, tissue temperature, output current and/or voltage, etc.) and provide feedback to the controller 24. Such sensors may include voltage and current sensors that are coupled to the output terminals 30 and 32 of the generator 20. In response to the sensor signals, the controller 24 controls the HVPS 27 and the RF output stage 28, which then adjusts the DC and the RF power supplies, respectively. The controller 24 also receives input signals from the input controls of the generator 20, the instrument 2, or the forceps 10. The controller 24 utilizes the input signals to adjust power outputted by the generator 20 and performs other control functions thereon.

Figure 4:
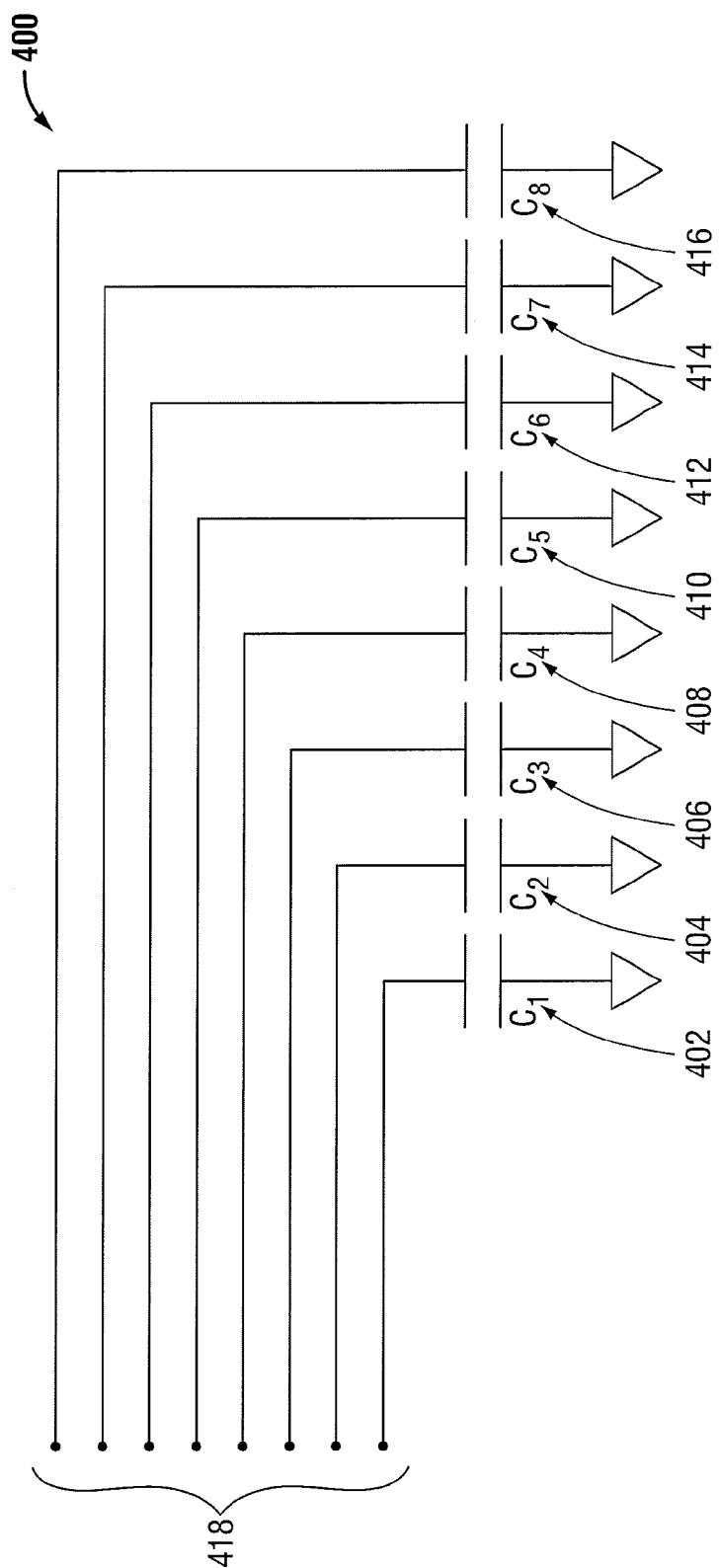
FIG. 4 is a schematic diagram of an identifying circuit according to an embodiment of the present disclosure.

FIG. 4 is a schematic diagram of an identifying circuit 400 according to an embodiment of the present disclosure. The identifying circuit 400 includes eight capacitive elements schematically represented by capacitors 402-414. Each of the capacitors 402-414 has a corresponding capacitance C1, C2 . . . C8, respectively. The capacitance-to-digital converter 36 can individually interrogate the capacitors 402-414 through interrogation lines 418 using the multiplexer 38 (see FIG. 3). FIGS. 4B and 4C show an embodiment of the identifying circuit 400 formed by depositing silver ink on a substrate.

The presently-disclosed capacitive elements may be formed by pad printing, silk-screening, lithography, laser printing, and/or suitable other processes. In some embodiments, described below, capacitive elements (e.g., capacitors 402-416 shown in FIGS. 4B, 4C and 5) may be formed using a direct write process, e.g., MICROPEN® Technologies' MICROPENNING®, to deposit material onto a surface. In general, the term "direct write" describes a printing or patterning method that employs a computerized, motion-controlled stage with a motionless pattern generating device to dispense flowable materials in a designed pattern onto a surface.

MICROPENNING® is a micro-capillary technology that uses a positive displacement method of pumping flowable materials, typically having a viscosity of between about 5 and about 500,000 centipoise, onto a surface. In some embodiments, using MICROPENNING® direct writing to precisely control the volume of flowable material (e.g., electrically-conductive ink) applied, in one or more layers, to the outer surface of a probe, results in the formation of patterns that meet specific tolerance requirements for an array of capacitive elements, e.g., to allow for probe identification.

FIG. 5A is a top view and FIG. 5B is the side view of the identifying circuit 400 formed by depositing metallic ink 402A and 402B on a substrate 417. Metallic ink 402A and 402B may be formed of any suitable electrically-conductive material, e.g., copper, gold, silver or other conductive metals having suitable conductivity values. Each of the capacitors 402-416 may be formed in this fashion. In other embodiments, other metallic inks or electrically-conductive materials may be deposited on the substrate 418 to form one or more capacitors 402-416. The substrate 418 may be made of a variety of inorganic and/or organic materials, including but not limited to silicon-based compounds, glass, quartz, sapphire, ceramic, polyimide (e.g., KAPTON®), polyester (e.g., MYLAR®), polyethylene terephthalate (PET), plastics. In some embodiments, the substrate 418 may be made of a composite material commercially available under the trademark POLYMED® offered by Polygon Company.

In some embodiments, the identifying circuit 400 may be formed, patterned or otherwise deposited on the outer surface of an energy applicator or probe. In some embodiments, the identifying circuit 400 may be formed using a direct write process, e.g., MICROPEN® Technologies' MICROPENNING®, or other suitable material deposition technology.

In the case of a parallel plate geometry, the capacitance of each of the capacitors 402-416 may be derived by Formula (1):

$$C = \frac{A\varepsilon_0 \varepsilon_r}{d}, \qquad (1)$$

where C is the capacitance of the capacitor, A is the area of the deposited ink on a side of the substrate 418, $\varepsilon_0$ is the permittivity constant, $\varepsilon_r$ is the dielectric constant of the substrate 418, and d is the distance between the two ink depositions, e.g., the distance between ink deposit 402A and 402B. In accordance with various embodiments of the present disclosure, the design of the capacitors may not be in a parallel plate geometry, and the capacitance of each of the capacitors 402-416 may be defined generally by Formula (2):

$$C = \frac{Q}{V}, \qquad (2)$$

where C is the capacitance of the capacitor, Q is charge, and V is voltage.

The areas of the deposited ink 402A-416A, and 402B-416B may be selected to correspond to a number. In some embodiments, the dimensions (e.g., the area A) of the ink deposited of the capacitors 402-416 may be selected so that each of the capacitors 402-416 has a capacitance that corresponds to a number such that the generator 20 (FIG. 3) can identify the instrument via the identifying circuit 400. Additionally or alternatively, the distance between the two ink depositions may be varied to vary the capacitance of the capacitive elements.

FIG. 5 shows a microwave surgical instrument 500 having an identifying circuit 400 according to an embodiment of the present disclosure. The identifying circuit 400 is coupled to, deposited on, or is otherwise attached to the outer sleeve of the microwave surgical instrument 500 such that the microwave generator can interrogate the identifying circuit 400.

Figure 6A:
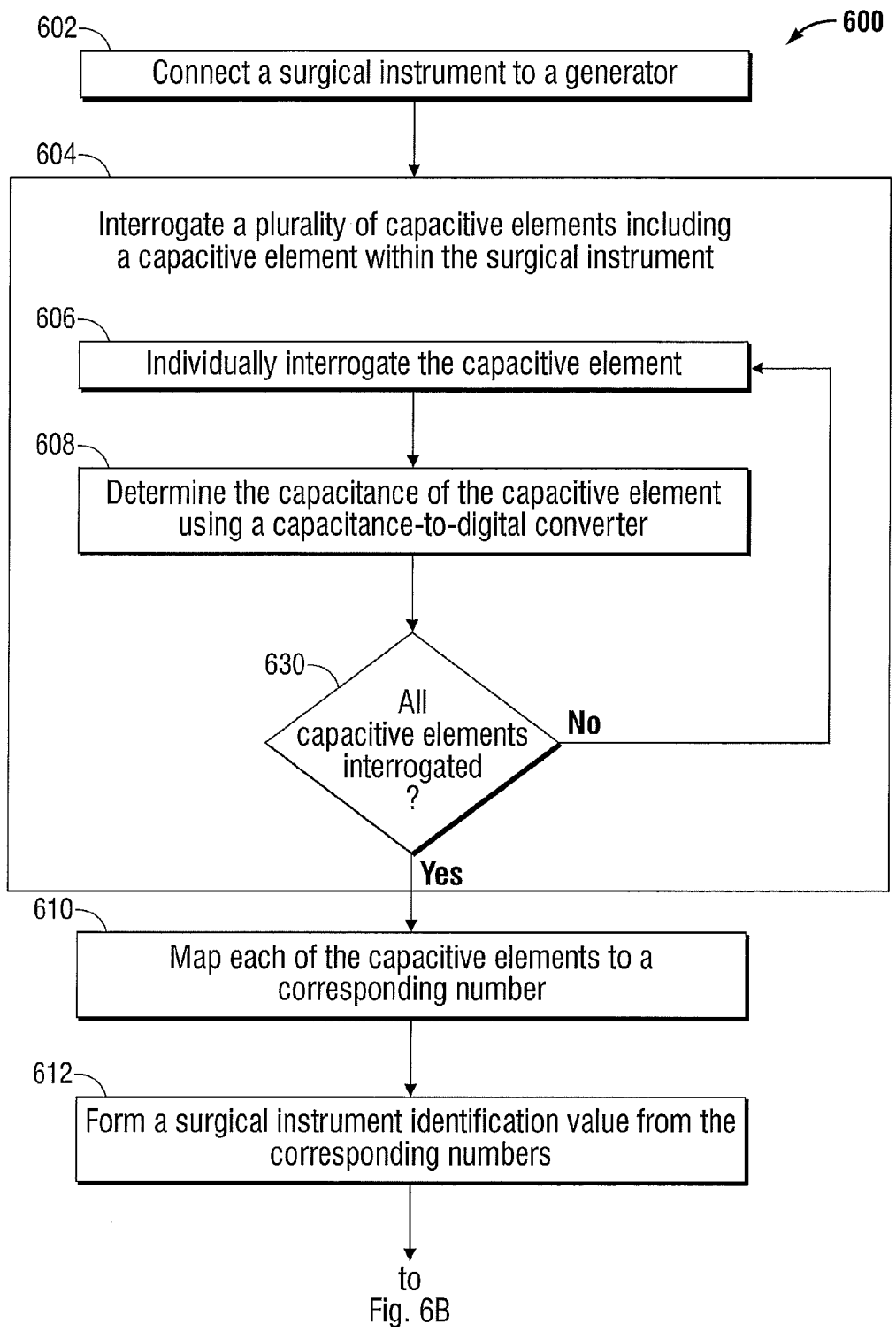
FIGS. 6A and 6B are flowcharts illustrating a method for identifying a surgical instrument according to an embodiment of the present disclosure.
Figure 6B:
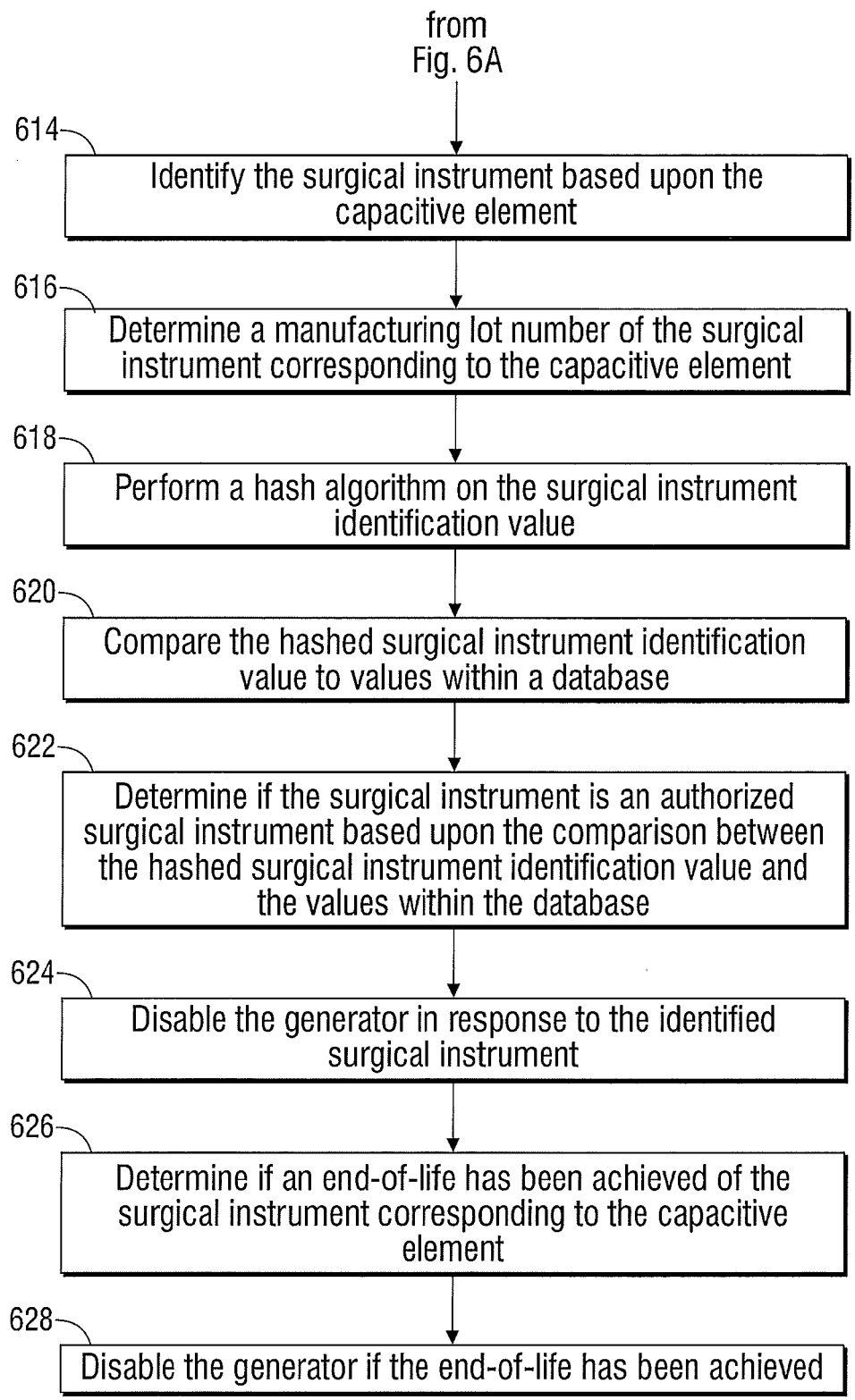

FIGS. 6A and 6B are flowcharts illustrating a method 600 of identifying a surgical instrument according to an embodiment of the present disclosure. In step 602, a surgical instrument is connected to a generator, e.g., generator 20. In step 604, a plurality of capacitive elements is interrogated including the capacitive element within the surgical instrument of step 602. Step 604 includes steps 606 and 608, and a decision step 630.

In step 606, a capacitive element is individually interrogated, e.g., the multiplexer 39 individually interrogates a capacitive element of capacitive elements 29. In step 608, the capacitance of the capacitive element is determined using a capacitance-to-digital converter. In decision step 630, it is determined if all of the capacitive elements 29 have been interrogated. If it is determined, in step 630, that not all of the capacitive elements 29 have been interrogated, then the method 600 repeats steps 606 and 608 until all of the capacitive elements 29 have been interrogated.

In step 610, each of the capacitive elements 29 is mapped to a corresponding number. In step 612, a surgical instrument identification value is formed from the corresponding numbers, e.g., by concatenating all of the corresponding numbers of all of the capacitive elements. In step 614, the surgical instrument is identified based upon the corresponding number from the capacitive element 29, e.g., using the surgical instrument identification value. In step 616, a manufacturing lot number of the surgical instrument corresponding to the capacitive element 29 is determined, e.g., using the surgical instrument identification value. In step 618, a hash algorithm is performed on the surgical instrument identification value. In step 620, the hashed surgical instrument identification value is compared to values within a database. In step 622, it is determined if the surgical instrument is an authorized surgical instrument based upon the comparison between the hashed surgical instrument identification value and the values within the database.

In step 624, the generator is disabled if the identified surgical instrument is an unauthorized surgical instrument or the lot number does not correspond to predetermined criteria. In step 646, it is determined if an end-of-life has been achieved by the surgical instrument corresponding to the capacitive element based upon a threshold value, e.g., disposable instrument=1. In step 628, the generator is disabled if the end-of-life has been achieved, e.g., the surgical instrument has been used a predetermined number of times.

FIG. 7 shows a microwave surgical instrument (shown generally as 700) according to an embodiment of the present disclosure. Microwave surgical instrument 700 generally includes an energy applicator or probe 701 including an elongate member 710 defining a longitudinal axis "A-A" and including a distal end 715. In some embodiments, the elongate member 710 may include a cooling jacket 714 and may be formed of any suitable material, e.g., POLYMED™ composite material tubing. In some embodiments, at least a portion of the cooling jacket 714 has an inner diameter that is larger than the outer diameter of an antenna assembly (not shown) thereby defining a tubular fluid lumen 712.

Microwave surgical instrument 700 may be provided with an end cap or tapered portion 750, e.g., disposed at the distal end 715 of the elongate member 710, which may terminate in a sharp tip to allow for insertion into tissue with minimal resistance. One example of a straight probe with a sharp tip that may be suitable for use as the probe 701 is commercially available under the trademark EVIDENT™ offered by Covidien Surgical Solutions, Boulder, Colo. The end cap or tapered portion 750 may include other shapes, such as, for example, a tip that is rounded, flat, square, hexagonal, or cylindroconical.

Figure 9:
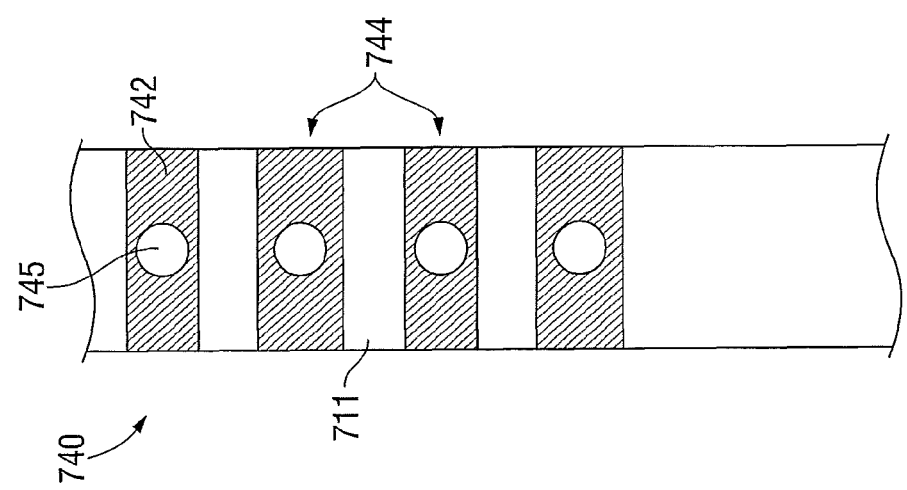
FIG. 9 is an enlarged view of the indicated area of detail of FIG. 7 showing a portion of the identifying circuit disposed on the outer surface of the instrument of FIG. 7 according to an embodiment of the present disclosure.

A first configuration of electrically-conductive traces (shown generally as 740 in FIGS. 7 and 9) is formed, patterned or otherwise deposited on a first portion 720 of the outer surface 711 of the probe 701. The first configuration 740 of electrically-conductive traces includes a plurality of individual traces 744, and may be formed from electrically-conductive ink 742, e.g., ink including electrically-conductive (e.g., silver) particles. One or more of the electrically-conductive traces 744 may include one or more element connections 745. In some embodiments, as shown in FIG. 9, each element connection 745 may be circular shaped, and may define pogo-pin or other isolated electrical connection. The shape and size of the element connections 745 may be varied from the configuration depicted in FIG. 9.

Figure 10:
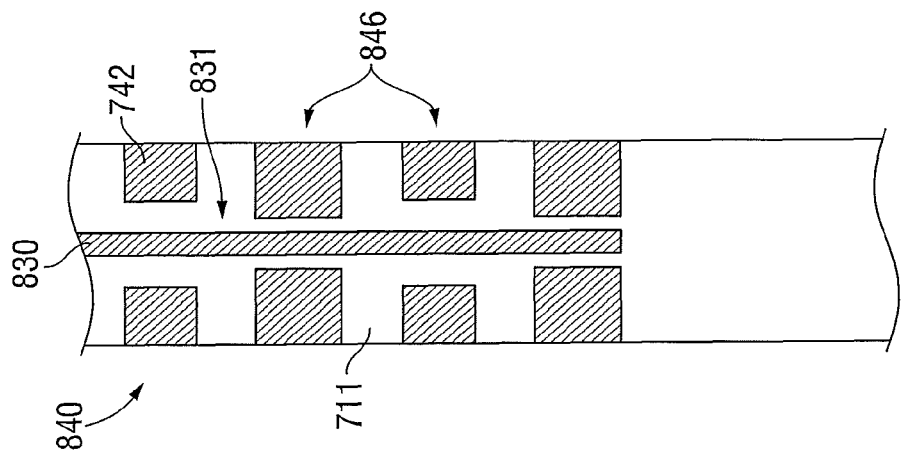
FIG. 10 is an enlarged view of the indicated area of detail of FIG. 8 showing a portion of the identifying circuit disposed on the outer surface of the instrument of FIG. 8 according to an embodiment of the present disclosure.

In FIG. 8, the microwave surgical instrument 700 of FIG. 7 is shown rotated 180 degrees about its longitudinal axis "A-A". A second configuration of electrically-conductive traces (shown generally as 840 in FIGS. 8 and 10) is formed, patterned or otherwise deposited on a second portion 820 of the outer surface 711 of the probe 701. The second configuration 840 of electrically-conductive traces may include the end portions 846 of the plurality of traces 744, and may be formed from electrically-conductive ink 742. The second configuration 840 may additionally include a ground trace 830. In some embodiments, as shown in FIGS. 8 and 10, the ground trace 830 includes a first portion 831 (FIG. 10) disposed between and spaced apart from the end portions 846 and a second portion 832 (FIG. 8) extending proximally along the longitudinal axis "A-A". The shape and size of the end portions 846 and the ground trace 830 may be varied from the configuration depicted in FIGS. 8 and 10.

As best shown in FIGS. 9 and 10, the plurality of traces 744 and the end portions 846 thereof are sized to have different capacitive values with respect to the ground trace 830. In some embodiments, the first configuration 740 of electrically-conductive traces and the second configuration 840 of electrically-conductive traces together form an identifying circuit of the probe 701.

In some embodiments, the first configuration 740 and/or the second configuration 840 may be formed using a direct write process, e.g., MICROPEN® Technologies' MICRO-PENNING®, to deposit material, e.g., electrically-conductive ink 742, onto one or more portions of the outer surface 711 of the probe 701.

The above-described surgical instruments including one or more identifying circuits may be suitable for utilization with endoscopic surgical procedures and/or hand-assisted, endoscopic and laparoscopic surgical procedures. The above-described surgical instruments including one or more identifying circuits may be suitable for utilization in open surgical applications. The above-described method of identifying a surgical instrument may be used to identify a variety of surgical instruments, e.g., bipolar and monopolar electrosurgical instruments.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A method for identifying a surgical instrument, the method comprising:
   connecting the surgical instrument to a generator;
   measuring a plurality of capacitance values of each of a plurality of capacitive elements formed on an outer surface of the surgical instrument;
   mapping each of the plurality of capacitance values to a corresponding value;
   sequentially concatenating each of the corresponding values to generate a surgical instrument identification value; and
   identifying the surgical instrument based on the generated surgical instrument identification value.

2. The method according to claim 1, wherein measuring a plurality of capacitance values includes interrogating the plurality of capacitive elements.

3. The method according to claim 1, further comprising performing a hash algorithm on the surgical instrument identification value.

4. The method according to claim 3, further comprising comparing the hashed surgical instrument identification value to values within a database.

5. The method according to claim 4, further comprising determining if the surgical instrument is an authorized surgical instrument based upon the comparison between the hashed surgical instrument identification value and the values within the database.

6. The method according to claim 1, wherein measuring a plurality of capacitance values includes individually interrogating each of the plurality of capacitive elements.

7. The method according to claim 1, further comprising disabling the generator in response to the identified surgical instrument.

8. The method according to claim 1, further comprising determining if an end-of-life has been achieved of the identified surgical instrument.

9. The method according to claim 1, further comprising determining a manufacturing lot number of the identified surgical instrument.

10. The method according to claim 1, wherein measuring a plurality of capacitance values includes determining a capacitance of each of the plurality of capacitive elements using a capacitance-to-digital converter.

* * * * *